United States Patent
Eckhardt et al.

(10) Patent No.: US 11,225,500 B2
(45) Date of Patent: Jan. 18, 2022

(54) SYNTHESIS OF 1:1:1 CO-CRYSTAL OF 1-CYANO-2-(4-CYCLOPROPYL-BENZYL)-4-(β-D-GLUCOPYRANOS-1-YL)-BENZENE, L-PROLINE AND WATER

(71) Applicant: Boehringer Ingelheim Vetmedica GmbH, Ingelheim am Rhein (DE)

(72) Inventors: Matthias Eckhardt, Biberach an der Riss (DE); Monika Brink, Gau-Algesheim (DE); Frank Himmelsbach, Mittelbiberach (DE); Stefan Sahli, Zofingen (CH); Chutian Shu, Pudong District (CN); Xiao-Jun Wang, Ridgefield, CT (US); Beat Theodor Weber, Zofingen (CH); Bing-Shiou Yang, Southbury, CT (US)

( * ) Notice: Subject to any disclaimer, the term of this patent is extended or adjusted under 35 U.S.C. 154(b) by 0 days.

(21) Appl. No.: 16/771,717

(22) PCT Filed: Dec. 17, 2018

(86) PCT No.: PCT/EP2018/085193
§ 371 (c)(1),
(2) Date: Jun. 11, 2020

(87) PCT Pub. No.: WO2019/121509
PCT Pub. Date: Jun. 27, 2019

(65) Prior Publication Data
US 2021/0139520 A1 May 13, 2021

(30) Foreign Application Priority Data
Dec. 19, 2017 (EP) .................... 17208315

(51) Int. Cl.
*C07H 1/00* (2006.01)
*C07C 69/614* (2006.01)
*C07C 291/00* (2006.01)
*C07H 7/04* (2006.01)

(52) U.S. Cl.
CPC ............. *C07H 1/00* (2013.01); *C07C 69/614* (2013.01); *C07C 291/00* (2013.01); *C07H 7/04* (2013.01); *C07C 2601/16* (2017.05)

(58) Field of Classification Search
CPC ...... C07H 1/00; C07D 309/10; C07C 69/614; C07C 291/00
See application file for complete search history.

(56) References Cited

U.S. PATENT DOCUMENTS

2007/0259821 A1* 11/2007 Eckhardt ............... A61P 3/06
514/23
2015/0272977 A1* 10/2015 Reiche ................. A61K 31/382
514/24

FOREIGN PATENT DOCUMENTS

| WO | 2007093610 | 8/2007 |
| WO | 2007128749 | 11/2007 |
| WO | 2014016381 | 1/2014 |

OTHER PUBLICATIONS

Li-Yuan Bao et al.: "Progress and developments in the turbo Grignard reagent i—PrMgCl—LiCl"; Chemical Communications, vol. 51, No. 32, 2015, p. 6884-6900.
Hynes J B et al.: "Further studies on the synthesis of quinazolines . . . "; Journal of Heterocyclic chemistry, vol. 28, No. 5, Aug. 1991, p. 1357-1363.
Unsinn A et al.: "A Convenient Alumination of Functionalized Aromatics by by using . . . "; Chemistry, vol. 19, No. 43, Oct. 18, 2013, p. 14687-14696.
Wolfe J P et al.: "Improved Functional Group Compatibility in the Palladium-Catalyzed . . . "; Tetrahedron Letters, vol. 38, No. 36, Sep. 8, 1997, p. 6359-6362.
International Search Report for PCT/EP2018/085193, dated Jun. 27, 2019, 7 pages.
Written Opinion of the International Search Authority for PCT/EP2018/085193, dated Jun. 23, 2020, 9 pages.

* cited by examiner

*Primary Examiner* — Jonathan S Lau
(74) *Attorney, Agent, or Firm* — Steffan Finnegan

(57) ABSTRACT

The invention relates to a process for the manufacture of the crystalline compound according to formula (I) comprising the steps (a) deacetylating the final intermediate (FI), (b) forming the crystalline compound according to formula (I) by reacting the deacetylated final intermediate of step (a) with L-proline and water and isolating the final reaction product; processes of manufacturing intermediates thereof; process intermediates and their uses in the processes according to the present invention.

11 Claims, No Drawings

SYNTHESIS OF 1:1:1 CO-CRYSTAL OF 1-CYANO-2-(4-CYCLOPROPYL-BENZYL)-4-(β-D-GLUCOPYRANOS-1-YL)-BENZENE, L-PROLINE AND WATER

FIELD OF THE INVENTION

The invention relates to the field of chemistry, particularly synthetic chemistry. In particular, the invention relates to the synthesis of crystalline 1-cyano-2-(4-cyclopropyl-benzyl)-4-(β-D-glucopyranos-1-yl)-benzene L-proline monohydrate, more particular to the 1:1:1 co-crystal of all three crystal components 1-cyano-2-(4-cyclopropyl-benzyl)-4-(β-D-glucopyranos-1-yl)-benzene, L-proline and water.

BACKGROUND OF THE INVENTION

WO 2007/093610 describes glucopyranosyl-substituted benzonitrile derivatives, pharmaceutical compositions containing such compounds, their medical uses as well as processes for their manufacture. It discloses among many other compounds also 1-cyano-2-(4-cyclopropyl-benzyl)-4-(β-D-glucopyranos-1-yl)-benzene.

WO 2007/128749 relates to glucopyranosyl-substituted benzonitrile derivatives, pharmaceutical compositions containing such compounds, their medical uses as well as processes for their manufacture. Among many other compounds it also discloses 1-cyano-2-(4-cyclopropyl-benzyl)-4-(β-D-glucopyranos-1-yl)-benzene.

WO 2014/016381 describes crystalline complexes of 1-cyano-2-(4-cyclopropyl-benzyl)-4-(β-D-glucopyranos-1-yl)-benzene with natural amino acids, methods for the preparation thereof as well as the use thereof for preparing medicaments. Although the WO publication describes crystalline 1-cyano-2-(4-cyclopropyl-benzyl)-4-(β-D-glucopyranos-1-yl)-benzene L-proline it does not explicitly mention 1-cyano-2-(4-cyclopropyl-benzyl)-4-(β-D-glucopyranos-1-yl)-benzene L-proline monohydrate.

Further prior art is as follows:

Li-Yuan Bao et al. (Chem. Commun. 2015, 32: 6884-6900), who review the progress and developments in the turbo Grignard reagent i-PrMgCl*LiCl.

The disadvantages of the prior art are as follows:
- 1-cyano-2-(4-cyclopropyl-benzyl)-4-(β-D-glucopyranos-1-yl)-benzene as a crude substance is an amorphous oil, which cannot be handled technically and in commercial scale without further processing/modification
- complex synthesis 1-cyano-2-(4-cyclopropyl-benzyl)-4-(β-D-glucopyranos-1-yl)-benzene with numerous intermediate steps non-commercially available starting material requires synthesis of precursors for the final synthesis of 1-cyano-2-(4-cyclopropyl-benzyl)-4-(β-D-glucopyranos-1-yl)-benzene The objective underlying the present invention is therefore to provide a synthesis process which overcomes the problems of the prior art as described above.

SUMMARY OF THE INVENTION

The present invention concerns in one aspect a process for the manufacture of the crystalline compound 1-cyano-2-(4-cyclopropyl-benzyl)-4-(β-D-glucopyranos-1-yl)-benzene L-proline monohydrate according to formula (I) comprising the steps:

(a) deacetylating the final intermediate (FI);

(b) forming the crystalline compound according to formula (I) by reacting the deacetylated final intermediate of step (a) with L-proline and water to enable isolation of the final reaction product.

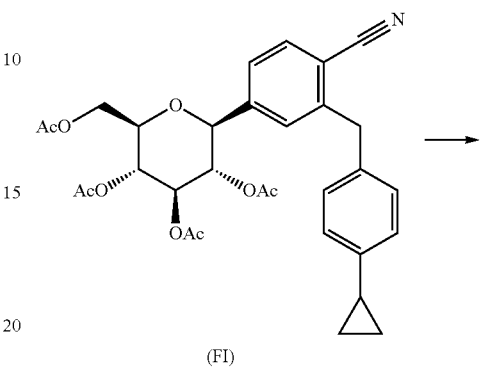

(FI)

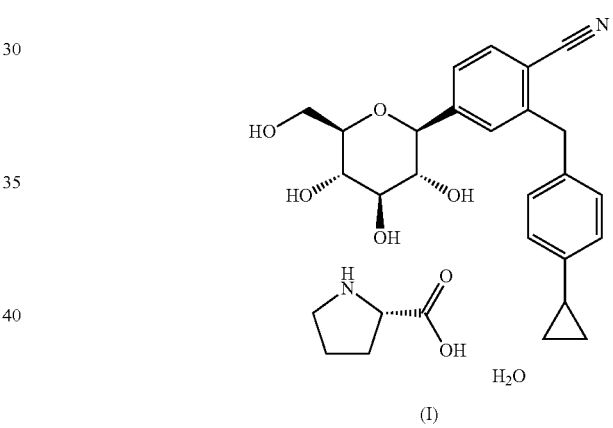

(I)

In another aspect the present invention concerns a process for the manufacture of final intermediate (FI) comprising the steps:

(a) reacting intermediate I1, wherein X is Br or I, with at least one metalation agent, preferably Turbo-Grignard (iPrMgCl*LiCl), and subsequently adding the reaction product of such metalation to intermediate I2, wherein PG is a protection group, preferably trimethylsilyl (TMS), to yield intermediate I3;

(b) treating intermediate I3 with methanol to yield intermediate I4;

(c) reducing intermediate I4 with a reduction agent, preferably a silane, more preferably triethylsilane, to yield intermediate I5;

(d) acetylating intermediate I5 to yield final intermediate FI;

wherein preferably at least one, more preferably all, of intermediates I3, I4 and/or I5 is/are not isolated and/or purified before further processing, i.e. performing steps (b), (c) and/or (d), respectively.

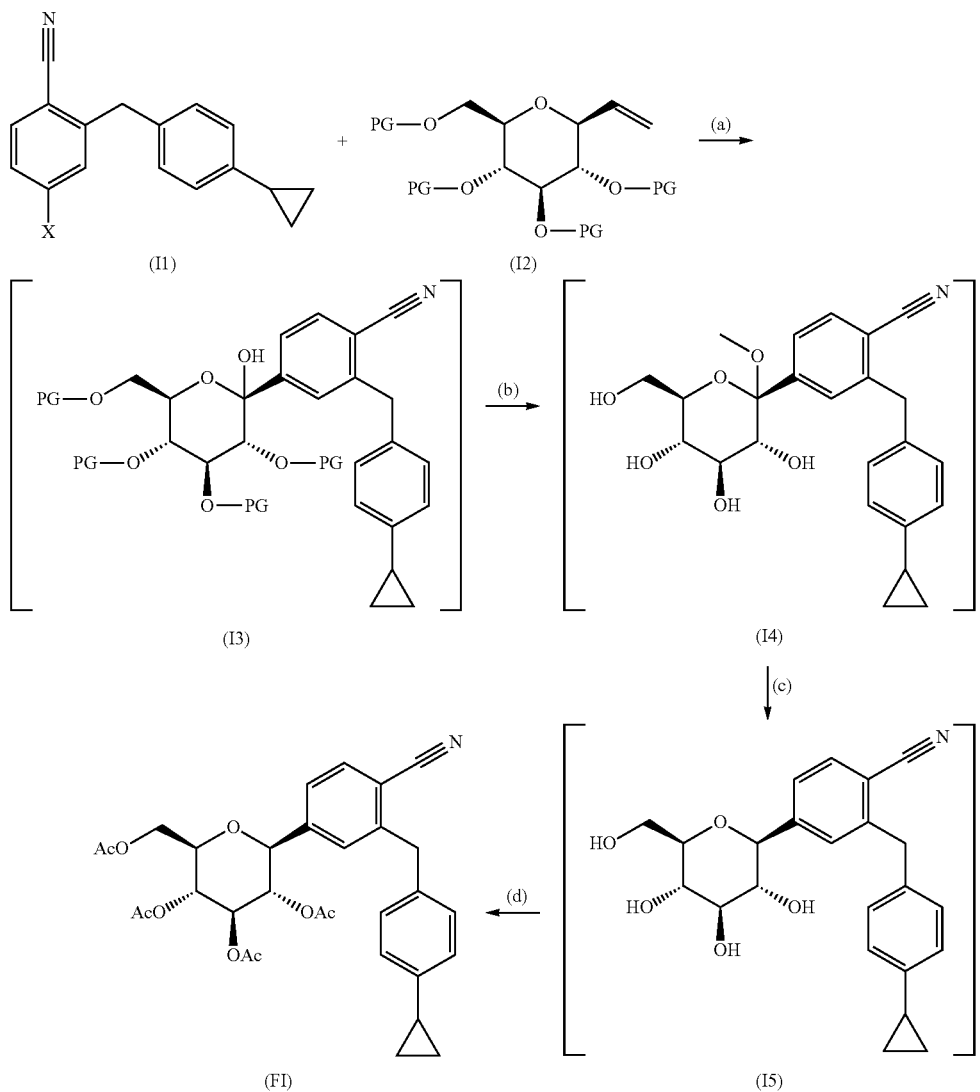

In a further aspect the present invention concerns a process for the manufacture of final intermediate (FI) comprising the steps:

(a) reacting intermediate I1, wherein X is Br or I, with at least one metalation agent, preferably Turbo-Grignard (iPrMgCl*LiCl), and subsequently adding the reaction product of such metalation to intermediate I2, wherein PG is a protection group, preferably trimethylsilyl (TMS), to yield intermediate I3;

(b) treating intermediate I3 with methanol to yield intermediate I4;

(c) acetylating intermediate I4 to yield intermediate I6;

(d) reducing intermediate I6 with a reduction agent, preferably a silane, more preferably triethylsilane, to yield final intermediate FI;

wherein preferably at least one, more preferably all, of intermediates I3, I4 and/or I6 is/are not isolated and/or purified before further processing, i.e. performing steps (b), (c) and/or (d), respectively.

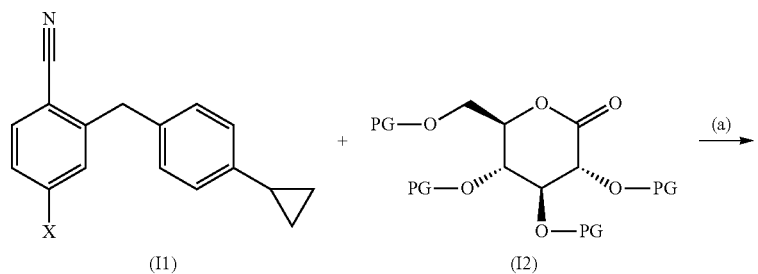

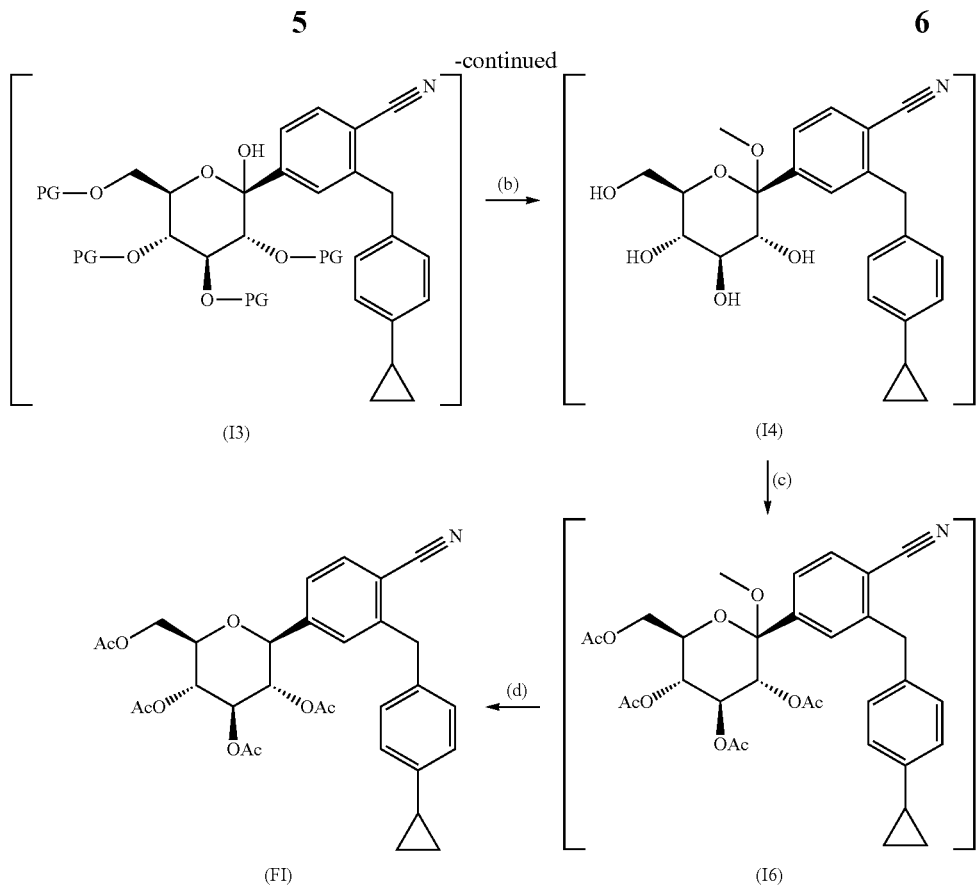

In yet another aspect the present invention concerns a process for the manufacture of intermediate I1 comprising the steps:
(a) reacting intermediate I7 with intermediate I8, wherein X is Br or I and wherein Hal is F or Cl, in the presence of a base, preferably potassium t-butoxide (KOtBu), to yield intermediate I1;
(b) isolating intermediate I1 from the reaction mixture of step (a).

In yet another aspect the present invention concerns crystalline compound 1-cyano-2-(4-cyclopropyl-benzyl)-4-(β-D-glucopyranos-1-yl)-benzene L-proline monohydrate according to formula (I)

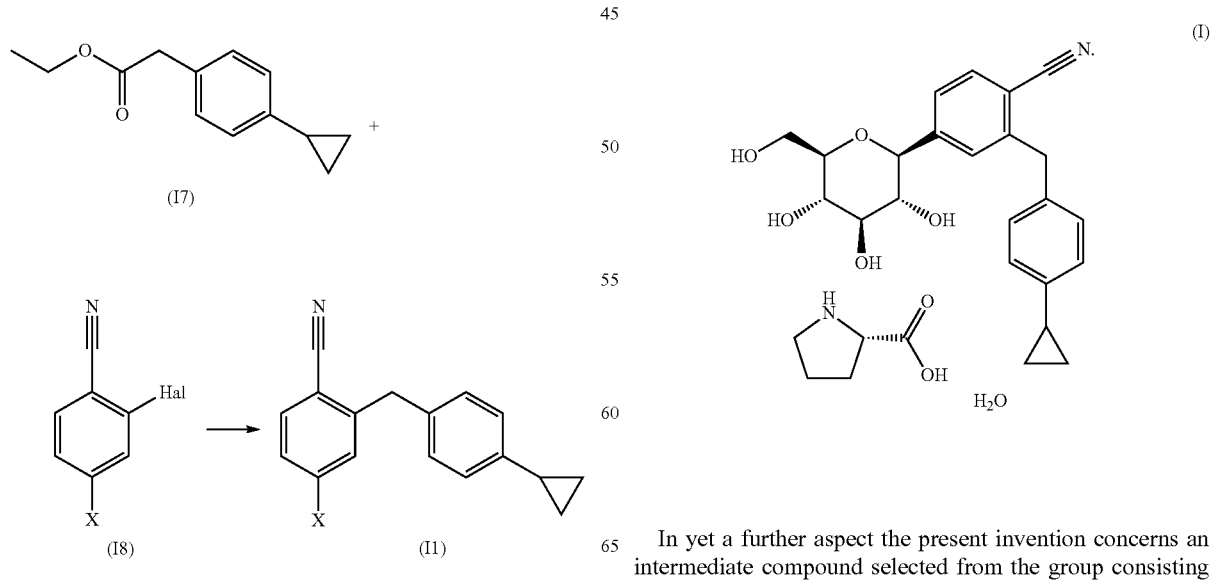

In yet a further aspect the present invention concerns an intermediate compound selected from the group consisting of intermediates (1) to (13):

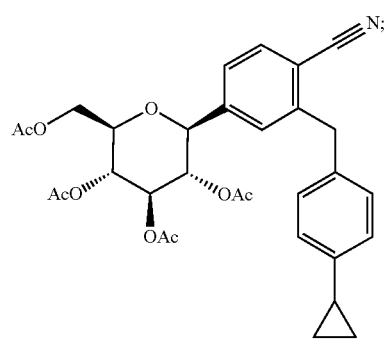
(1)
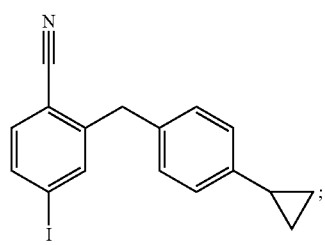
(2)
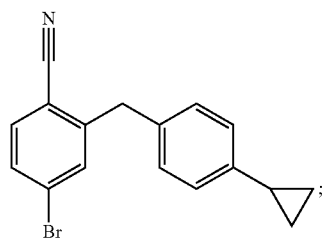
(3)
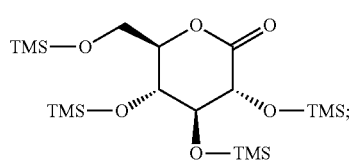
(4)
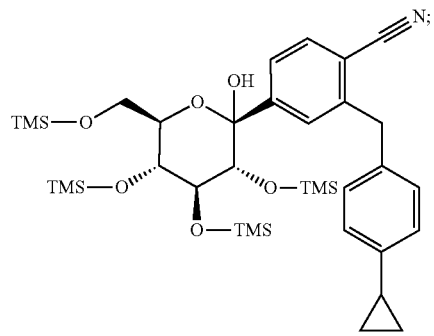
(5)
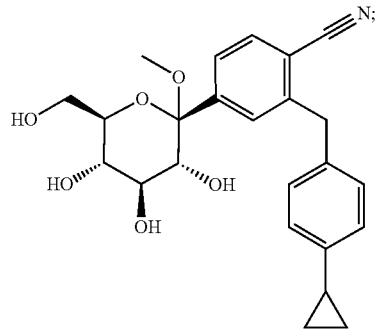
(6)
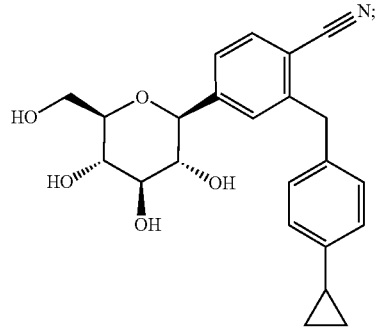
(7)
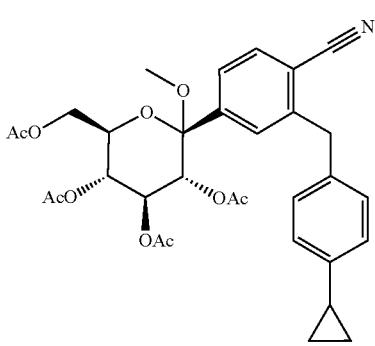
(8)
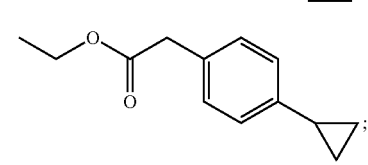
(9)
(10)
(11)
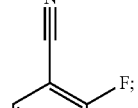

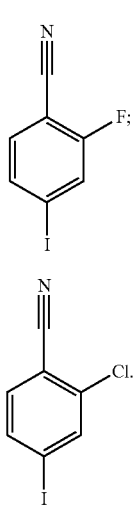

(12)

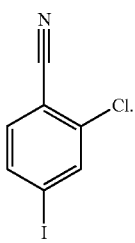

(13)

In yet another aspect the present invention concerns an intermediate compound selected from intermediate compounds (1) to (13) as herein disclosed obtainable by one or more processes according to the present invention as herein disclosed.

In yet a further aspect the present invention concerns the use of an intermediate compound selected from intermediate compounds (1) to (13) as herein disclosed in one or more processes according to the present invention as herein disclosed.

The advantages of the synthesis processes according to the present invention are as follows:
- 1:1:1 co-crystal can be technically handled in contrast to the oil form of the free compound, i.e. crystallized, isolated, characterized and further processed in commercial scale
- "non-obvious" chemistry: it was very difficult to develop a synthesis strategy comprising a molecule with a benzonitrile moiety—employing an organomagnesium or lithium compound as for the synthesis of non-cyanated glucosides can be troublesome since the nitrile moiety may interfere with the halogen-metal exchange and subsequent addition reaction
- shorter/more efficient/more economic synthesis route due to incorporating the cyano group in the aglycon from the beginning instead of introducing it afterwards from a halogenated, brominated or chlorinated, precursor in an extra synthesis step
- commercially available starting materials or starting materials that can be prepared easily.

DETAILED DESCRIPTION OF THE INVENTION

Before the embodiments of the present invention are described in further details it shall be noted that as used herein and in the appended claims, the singular forms "a", "an", and "the" include plural reference unless the context clearly dictates otherwise.

Unless defined otherwise, all technical and scientific terms used herein have the same meanings as commonly understood by one of ordinary skill in the art to which this invention belongs. All given ranges and values may vary by 1 to 5% unless indicated otherwise or known otherwise by the person skilled in the art, therefore, the term "about" was usually omitted from the description and claims Although any methods and materials similar or equivalent to those described herein can be used in the practice or testing of the present invention, the preferred methods, devices, and materials are now described. All publications mentioned herein are incorporated herein by reference for the purpose of describing and disclosing the substances, excipients, carriers, and methodologies as reported in the publications which might be used in connection with the invention. Nothing herein is to be construed as an admission that the invention is not entitled to antedate such disclosure by virtue of prior invention.

In the course of the present invention crystalline compound 1-cyano-2-(4-cyclopropyl-benzyl)-4-(β-D-glucopyranos-1-yl)-benzene L-proline monohydrate is herewith understood to be the 1:1:1 co-crystal of all three crystal components 1-cyano-2-(4-cyclopropyl-benzyl)-4-(β-D-glucopyranos-1-yl)-benzene, L-proline and water, as represented by formula (I):

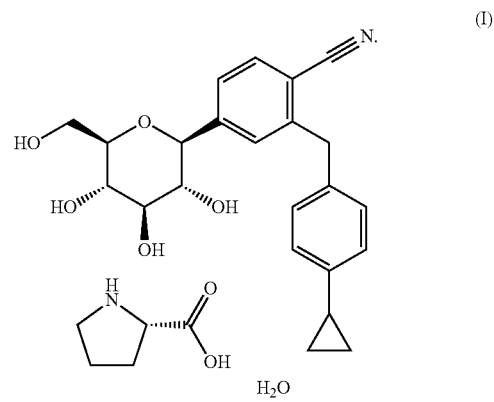

(I)

Such 1:1:1 co-crystal is physicochemically characterized in WO 2014/016381.

In a preferred embodiment the present invention provides for a process for the manufacture of the crystalline compound 1-cyano-2-(4-cyclopropyl-benzyl)-4-(β-D-glucopyranos-1-yl)-benzene L-proline monohydrate according to formula (I) comprising the steps
(a) deacetylating the final intermediate (FI);
(b) forming the crystalline compound according to formula (I) by reacting the deacetylated final intermediate of step (a) with L-proline and water and isolating the final reaction product;
wherein the deacetylation step (a) comprises the following steps:
(a1) reacting the final intermediate (FI) dissolved in at least one organic solvent, preferably methyl tetrahydrofuran (MeTHF), in the presence of a base, preferably NaOH, and water;
(a2) optionally, swapping the at least one organic solvent of the organic phase yielded in step (a1), preferably methyl tetrahydrofuran (MeTHF), to at least one different organic solvent, preferably 2-propanol, and optionally adding water.

Preferably, the crystalline compound forming step (b) further comprises the following steps:
(b1) adding L-proline, which is dissolved in the at least one different organic solvent, preferably 2-propanol, and water, to the water-organic phase mixture, preferably 2-propanol and water, yielded in step (a1) or optionally step (a2), and incubating such reaction mixture;

(b2) isolating the crystalline compound 1-cyano-2-(4-cyclopropyl-benzyl)-4-(β-D-glucopyranos-1-yl)-benzene L-proline monohydrate according to formula (I) from the reaction mixture of step (b1).

In another preferred embodiment the present invention provides for a process for the manufacture of final intermediate (FI) comprising the steps:

(a) reacting intermediate I1, wherein X is Br or I, with at least one metalation agent, preferably Turbo-Grignard (iPrMgCl*LiCl), and subsequently adding the reaction product of such metalation to intermediate I2, wherein PG is a protection group, preferably trimethylsilyl (TMS), to yield intermediate I3;

(b) treating intermediate I3 with methanol to yield intermediate I4;

(c) reducing intermediate I4 with a reduction agent, preferably a silane, more preferably triethylsilane, to yield intermediate I5;

(d) acetylating intermediate I5 to yield final intermediate FI;

wherein preferably at least one, more preferably all, of intermediates I3, I4 and/or I5 is/are not isolated and/or purified before further processing, i.e., performing steps (b), (c) and/or (d), respectively; and wherein X is I and/or PG is trimethylsilyl (TMS), preferably X is I and PG is trimethylsilyl (TMS).

In another preferred embodiment the present invention provides for a process for the manufacture of final intermediate (FI) comprising the steps:

(a) reacting intermediate I1, wherein X is Br or I, with at least one metalation agent, preferably Turbo-Grignard (iPrMgCl*LiCl), and subsequently adding the reaction product of such metalation to intermediate I2, wherein PG is a protection group, preferably trimethylsilyl (TMS), to yield intermediate I3;

(b) treating intermediate I3 with methanol to yield intermediate I4;

(c) acetylating intermediate I4 to yield intermediate I6;

(d) reducing intermediate I6 with a reduction agent, preferably a silane, more preferably triethylsilane, to yield final intermediate FI;

wherein preferably at least one, more preferably all, of intermediates I3, I4 and/or I6 is/are not isolated and/or purified before further processing, i.e., performing steps (b), (c) and/or (d), respectively; and wherein X is I and/or PG is trimethylsilyl (TMS), preferably X is I and PG is trimethylsilyl (TMS).

In principle, any suitable protection group known to the person skilled in the art can be employed. Exemplary protection groups (PG) according to the present invention are trimethylsilyl (TMS), triethylsilyl (TES), triisopropylsilyl (TIPS), tert-butyldimethylsilyl (TBS, TBDMS), tert-butyldiphenylsilyl (TBDPS), benzyl (Bn), 4-methoxybenzyl (PMB), 2-naphthylmethyl (Nap), 2-methoxyethoxymethyl (MEM), 2,2,2-trichloroethyl carbonyl (Troc), methyl and the like. Preferred protection group (PG) according to the present invention is trimethylsilyl (TMS).

With regard to the reduction agent, in principle any suitable reduction agent known to the person skilled in the art can be employed. Exemplary reduction agents according to the present invention are silanes, such as triethylsilane, tripropylsilane, triisopropylsilane or diphenylsilane, sodium borohydride, sodium cyanoborohydride, zinc borohydride, boranes, lithium aluminum hydride, diisobutylaluminum hydride and the like. Preferred reduction agent is a silane, more preferably triethylsilane.

In yet another preferred embodiment the present invention provides for a process for the manufacture of intermediate I1 comprising the steps:

(a) reacting intermediate I7 with intermediate I8, wherein X is Br or I and wherein Hal is F or Cl, in the presence of a base, preferably potassium t-butoxide (KOtBu), to yield intermediate I1;

(b) isolating intermediate I1 from the reaction mixture of step (a);

wherein X is I and/or Hal is F, preferably X is I and Hal is F.

In yet another preferred embodiment the present invention provides for an intermediate compound selected from the group consisting of:

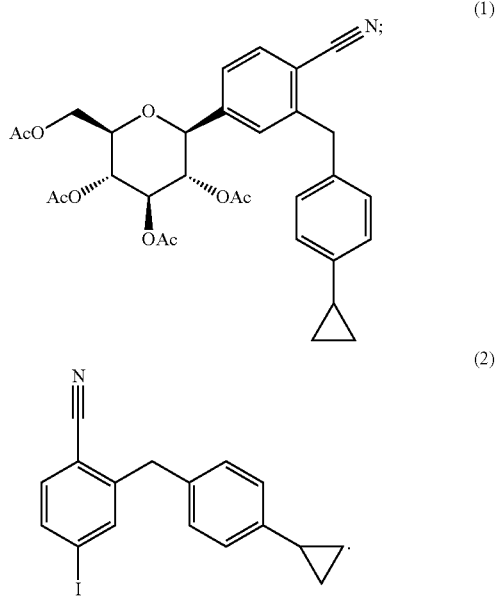

EXAMPLES

The following examples serve to further illustrate the present invention; but the same should not be construed as a limitation of the scope of the invention disclosed herein.

Example 1—Preparation of 1-cyano-2-(4-cyclopropyl-benzyl)-4-(β-D-glucopyranos-1-yl)-benzene L-proline monohydrate According to Formula (I) Starting from Final Intermediate FI 30 g Intermediate FI was dissolved in 130 g 2-methyltetrahydrofuran. 9.3 g NaOH (30% in water) was added and the resulting solution was heated to 50° C. for 3 hours, cooled to 5° C. and the pH adjusted to 9.3 using 1 M aqueous HCl-solution. The phases were separated and the organic phase was washed with water. The organic solvent was swapped to 2-propanol and 3.3 g water was added at room temperature. A solution of 6.3 g L-proline in 8.5 g water and 42 g 2-propanol was added at 23° C. within 4 h, and seeded during the addition. The resulting suspension was cooled to 5° C., stirred for 1 h, and the product filtered. After washing with a solvent mixture of 60 g 2-propanol and 3.5 g water, and drying in vacuo, the final crystalline compound had a purity of 100% (analyzed by HPLC) and overall yield was 87%.

Example 2—Preparation of Final Intermediate FI Starting from Intermediates I1 and I2—Variant A 628 mg Intermediate I1, X=Br, dissolved in 8 mL tetrahydrofuran (THF), was reacted during 15 minutes with 2.4 mL tert-butyllithium (1.7 M in pentane) at −100° C. 934 mg of intermediate I2 (PG=trimethylsilyl, TMS) dissolved in 5 mL THF was added and the reaction mixture has been kept at −80° C. After 1 hour the reaction was quenched with 14 mL saturated aqueous of ammonium chloride-solution followed by extraction with ethyl acetate, drying over magnesium sulfate and concentration of the solution. The residue was dissolved in 9.4 mL solvent mixture methanol and 0.32 mL methanesulfonic acid added the mixture kept at 55° C. After 16 hours the pH was adjusted to 8 by addition of saturated sodium bicarbonate solution, concentrated in vacuo. The residue was partitioned between ethyl acetate and saturated sodium chloride solution. The organic phase was dried over magnesium sulfate and concentrated in vacuo to get intermediate I4.

1400 mg residue containing intermediate I4 was reduced with 1.17 g triethylsilane and 1.6 g boron trifluoride diethyl etherate in a mixture of 4.5 g dichloromethane and 5 g acetonitrile at 22° c. for 1 h. The reaction mixture was added to 12 hg 2 N aqueous sodium hydroxide solution an extracted with TBME. The organic phase was concentrated in vacuo and treated trice with 7 g MeOH and evaporated to ⅕ volume. The residue was then dissolved in 8 g THF and the intermediate FI was obtained by acetylation with 2.2 g acetic anhydride, 2.5 g N-methylmorpholine and a catalytic amount of 4-(dimethylamino)-pyridine. Isolation and crystallization from aqueous methanol (1:1) gave the intermediate I1 at a purity of 98.4% and a total overall yield of 26%.

Example 3—Preparation of Final Intermediate FI Starting from Intermediates I1 and I2—Variant B Intermediate I4 has been obtained as described in example 2.

220 mg of intermediate I4 have been acetylated with 0.24 mL acetic anhydride, 390 mg N,N-diisopropylethylamine, and a catalytic amount of 4-(dimethylamino)-pyridine in 5 mL dichloromethane. After extractive aqueous work-up, drying over magnesium sulfate and evaporation in vacuo, 320 mg of the acetylated intermediate I6 was reduced in 4 mL acetonitrile with 0.19 mL, triethylsilane, 0.11 mL, boron trifluoride diethyl etherate and 1 equivalent water. Purity of intermediate FI was >85% and yield was 26%.

Example 4a—Preparation of Intermediate I1 Starting from Intermediates I7 and I8

In 6.6 g of intermediate I7, 8 g of intermediate I8 (Hal=F, X=I) were dissolved in 28.5 g tetrahydrofuran and 6.2 g dimethylformamide, and a solution of 8 g potassium tert-butoxide in 59 g tetrahydrofuran was added to the mixture at −20° C. and stirred for 1 h. The reaction was quenched by addition of 27.2 g water and 13.2 g 30% aqueous sodium hydroxide solution. The resulting mixture was then stirred at 55° c. for 16 h and cooled to 22° C. 10 g acetic acid and 25 g water were added, the phases separated and 67.5 g isopropyl acetate added to the organic phase. The organic phases was washed with 67 g 5% aqueous sodium chloride solution, and the solvent swapped to 2-propanol. The product was crystallized from 2-propanol by seeding and cooling to 15° C. The product was filtered and washed with 2-propanol to yield intermediate I1 in 97% purity and 50% yield.

Example 4b—Preparation of Intermediate I1 Starting from Intermediates I7 and I8

Example 4a has been repeated using intermediate I8 (Hal=F, X=Br). Overall yield is 47% and purity of the intermediate was >90%.

Example 5—Preparation of Intermediate I7

Intermediate I7 has been prepared by mixing cyclopropyl magnesium bromide (1.0 eq.), zinc chloride (1.3 eq.) and ethyl 2-(4-bromophenyl)acetate (1.0 eq.) in presence of triphenylphosphine (0.06 eq.) and palladium(II) acetate (0.05 eq.) in tetrahydrofuran at a temperature of 50° C. Extractive workup using ethyl acetate and water gave the crude product that was purified by distillation. Yield 70%. Purity >97.0%.

Example 6—Alternative Synthesis Route

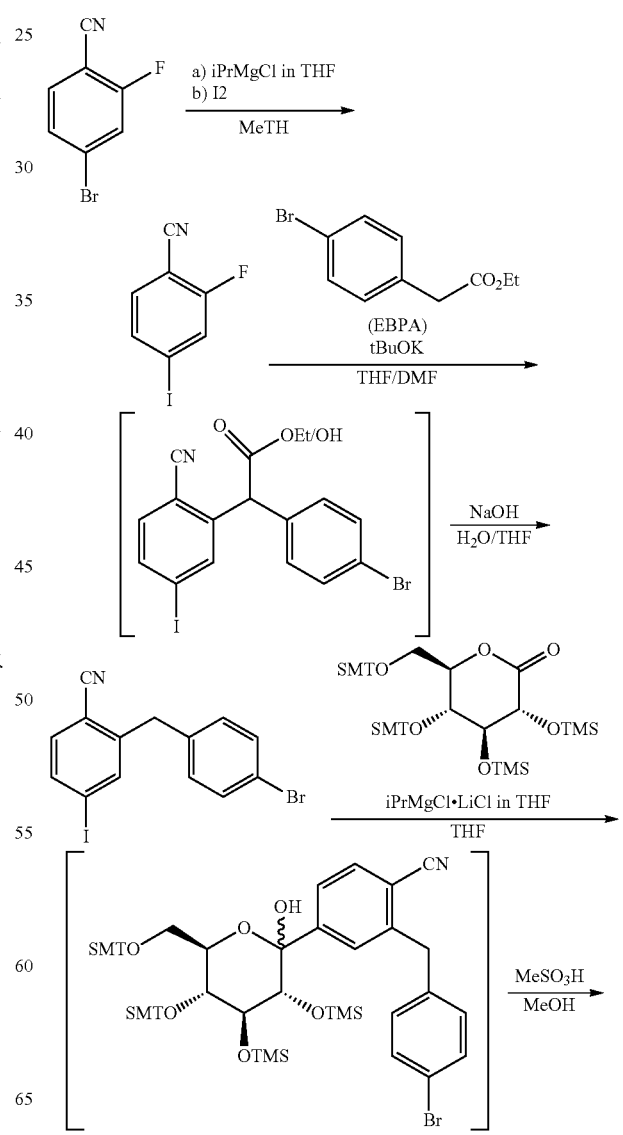

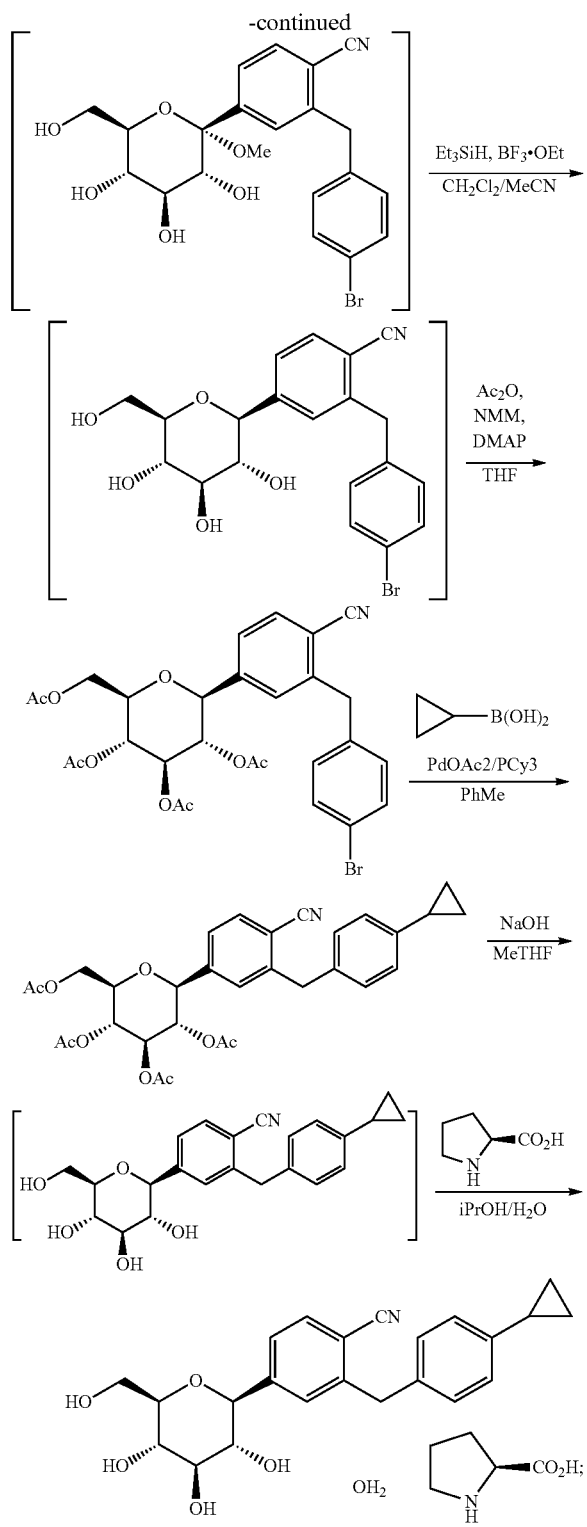

Abbreviations:
iPrMgCl=isopropylmagnesium chloride; I2=iodine; THF=tetrahydrofuran; MeTHF=2-methyl tetrahydrofuran; tBuOK=potassium tert-butoxide; DMF=dimethylformamide; NaOH=sodium hydroxide; iPrMgCl.LiCl=isopropylmagnesium chloride lithium chloride; TMS=trimethylsilyl; MeSO$_3$H=methanesulfonic acid; MeOH=methanol; Et$_3$SiH=triethylsilane; BF$_3$.OEt=boron trifluoride etherate; Ac$_2$O=acetic anhydride; NMM=N-methylmorpholine; DMAP=4-dimethylaminopyridine; Ac=Acetyl; PdOAc2=palladium(II) acetate; PCy3=tricyclohexylphosphine; PhMe=toluene; iPrOH=isopropanol.

Alternatively, final intermediate FI can by synthesized by installing the cyclopropyl moiety at a later stage in the synthesis as shown in the scheme above. Instead of employing compound 2, the corresponding aryl bromo iodobenzonitrile may be used. The aryl bromo iodobenzonitrile can be prepared by a nucleophilic aromatic substitution/decarboxylation coupling between 2-fluoro-4-iodobenzonitrile and ethyl-4-bromophenylacetate. The aryl bromo iodobenzonitrile can then be subjected to the same chemistry sequence of halogen-metal exchange/lactone addition/acidic methanol/reduction/acetylation. It is then necessary to install the cyclopropyl moiety of the isolated product from this sequence by a transition metal catalyzed reaction with an appropriate cyclopropyl species, such as cyclopropylboronic acid, to obtain final intermediate FI.

In detail, 2-fluoro-4-bromobenzonitrile is reacted with isopropylmagnesium chloride and iodine to yield 2-fluoro-4-iodobenzonitrile. Such yielded intermediate compound is then coupled with ethyl-4-bromophenylacetate and subsequently decarboxylated to yield 2-(4-bromobenzyl)-4-iodo-benzonitrile. 2-(4-bromobenzyl)-4-iodo-benzonitrile is then reacted with intermediate "I2" [PG=trimethylsilyl (TMS)] and reduced and acetylated in a chemical synthesis sequence of halogen-metal exchange/lactone addition/acidic reduction/acetylation analogously to the herein described and claimed process for the manufacture of final intermediate (FI), steps (b) and (c), with involved intermediates I3, I4 and I5 carrying a bromo substitution instead of the displayed cyclopropyl substitution at the distal benzyl moiety. At the end of this chemical synthesis sequence the cyclopropyl moiety is installed in the corresponding bromo analogue of final intermediate (FI) by means of a transition metal catalyzed reaction with an appropriate cyclopropyl species, such as cyclopropylboronic acid, to obtain final intermediate (FI). The final intermediate (FI) is then subjected to the process for the manufacture of the crystalline compound 1-cyano-2-(4-cyclopropyl-benzyl)-4-(β-D-glucopyranos-1-yl)-benzene L-proline monohydrate according to formula (I) as herein described and claimed.

REFERENCES (1) WO 2007/093610
(2) WO 2007/128749
(3) WO 2014/016381
(4) Li-Yuan Bao et al., Chem. Commun. 2015, 32: 6884-6900

The invention claimed is:
1. A process for the manufacture of final intermediate (FI) comprising the steps:
(a) reacting intermediate I1, wherein X is I, with at least one metalation agent, and subsequently adding the reaction product of such metalation to intermediate I2, wherein PG is a protection group, to yield intermediate I3;
(b) methylating intermediate I3 to yield intermediate I4;
(c) reducing intermediate I4 with a reduction agent to yield intermediate I5; and
(d) acetylating intermediate I5 to yield final intermediate FI;

wherein the intermediates I3, I4 and I5 are not isolated and/or purified before performing steps (b), (c) and/or (d), respectively:

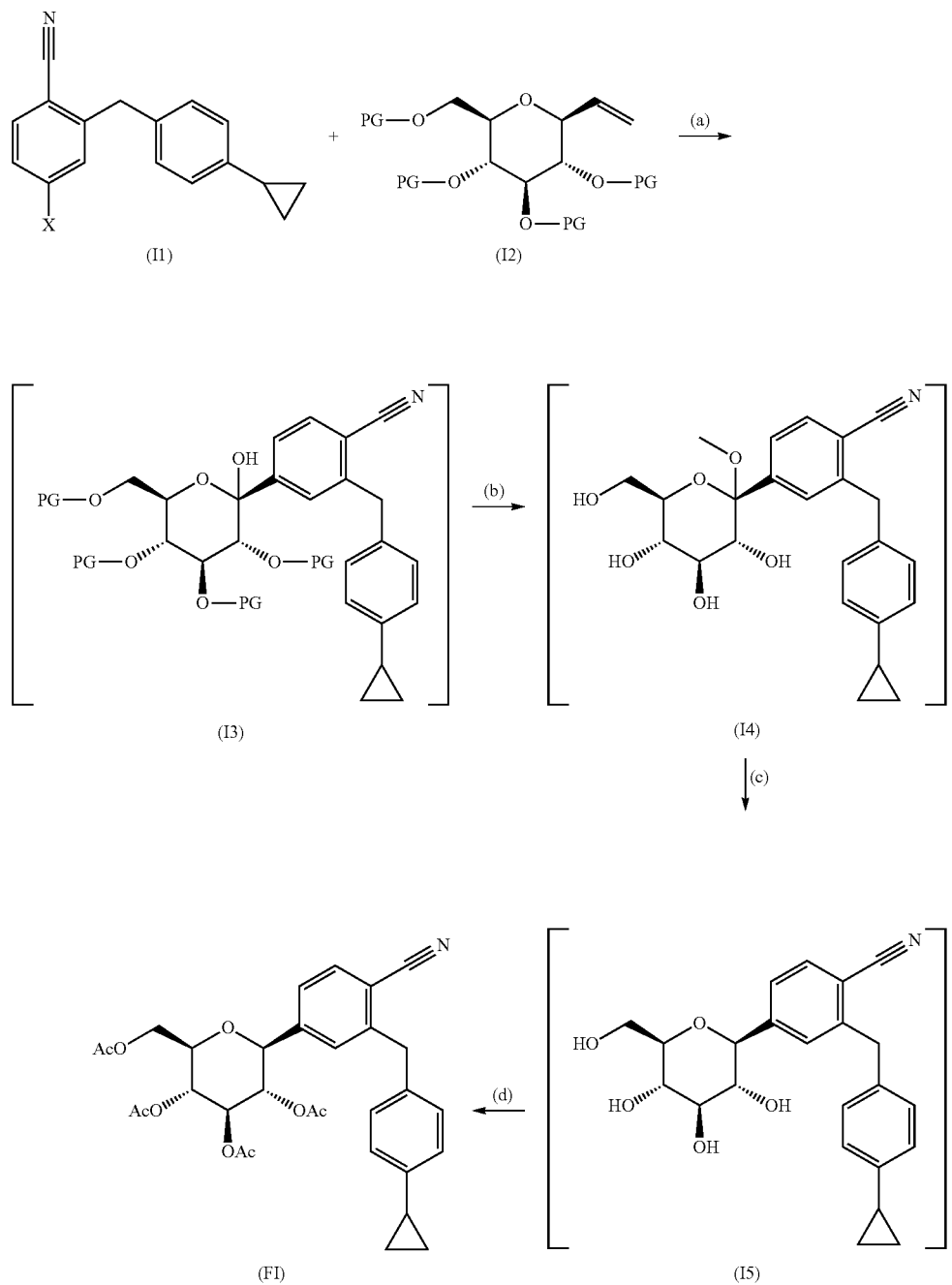

2. The process according to claim 1, wherein PG is trimethylsilyl (TMS).

3. The process according to claim 1, wherein the at least one metalation agent comprises Turbo-Grignard (iPrMgCl*LiCl).

4. The process according to claim 1, wherein the reduction agent comprises trimethylsilane.

5. A process for the manufacture of final intermediate (FI) comprising the steps:

(a) reacting intermediate I1, wherein X is I, with at least one metalation agent, and subsequently adding the reaction product of such metalation to intermediate I2, wherein PG is a protection group, to yield intermediate I3;

(b) methylating intermediate I3 to yield intermediate I4;

(c) acetylating intermediate I4 to yield intermediate I6;

(d) reducing intermediate I6 with a reduction agent to yield final intermediate FI;

wherein all of the intermediates I3, I4 and I6 are not isolated and/or purified before performing steps (b), (c) and/or (d), respectively:

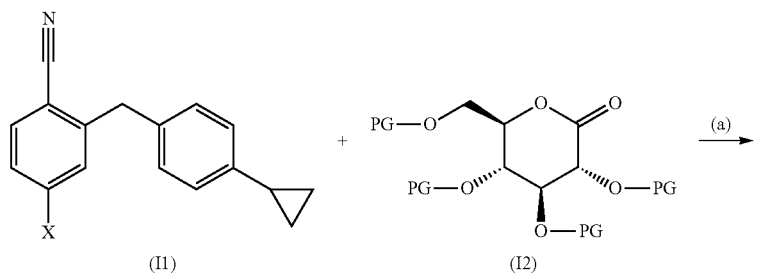

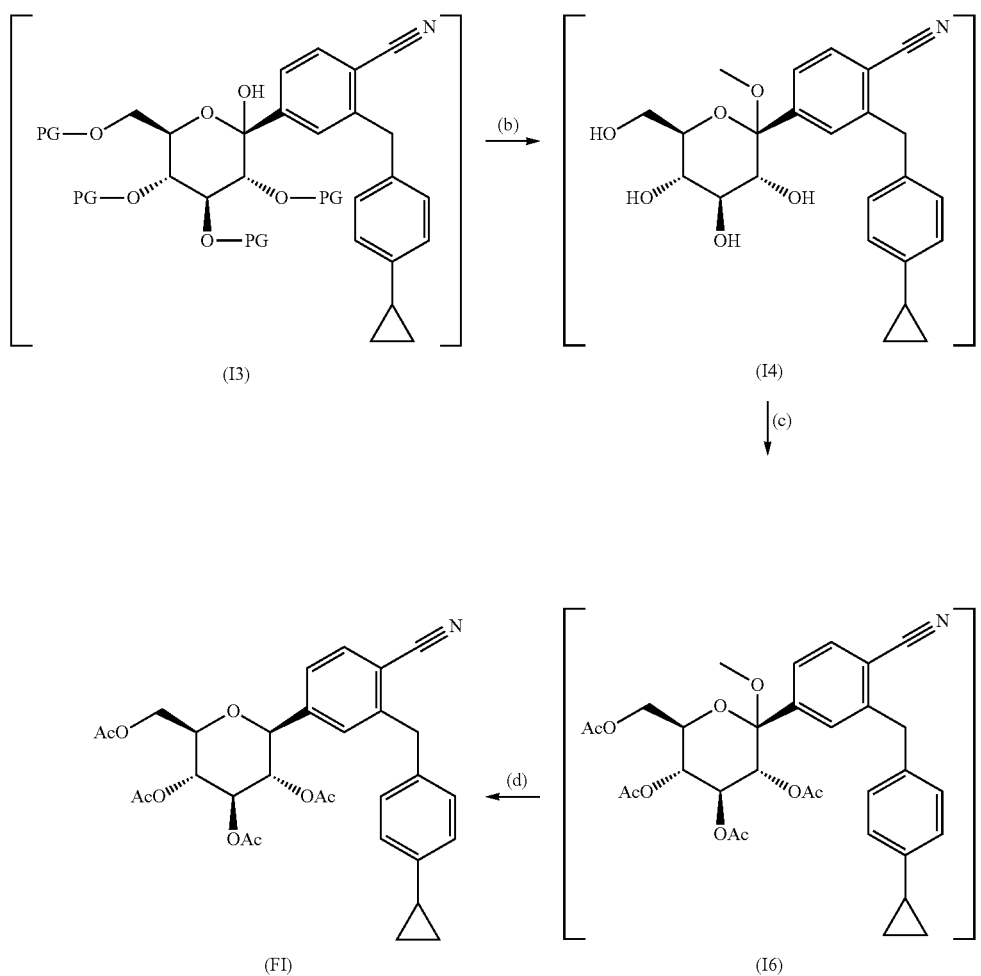

6. The process according to claim 5, wherein PG is trimethylsilyl (TMS).

7. The process according to claim 5, where the at least one metalation agent comprises Turbo-Grignard (iPrMgCl*LiCl).

8. The process according to claim 5, wherein the reduction agent comprises trimethylsilane.

9. A process for the manufacture of the crystalline compound 1-cyano-2-(4-cyclopropyl-benzyl)-4-(β-D-glucopyranos-1-yl)-benzene L-proline monohydrate according to formula (I)

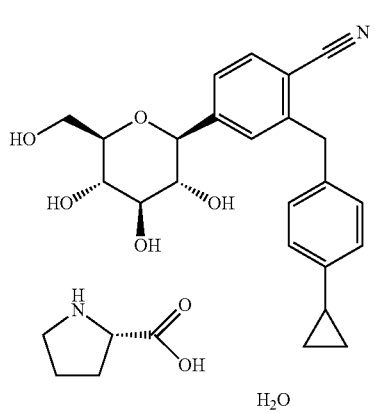

(I)

comprising the following steps:
(a) 2-fluoro-4-bromobenzonitrile is reacted with isopropylmagnesium chloride and iodine to yield 2-fluoro-4-iodobenzonitrile;
(b) 2-fluoro-4-iodobenzonitrile is then coupled with ethyl-4-bromophenylacetate and subsequently decarboxylated to yield 2-(4-bromobenzyl)-4-iodo-benzonitrile;
(c) 2-(4-bromobenzyl)-4-iodo-benzonitrile is then reacted with intermediate "I2" [PG=trimethylsilyl (TMS)] and reduced and acetylated in a chemical synthesis sequence of halogen-metal exchange/lactone addition/acidic reduction/acetylation according to claim 4, steps (b) and (c), with involved intermediates I3, I4 and I5 carrying a bromo substitution instead of the displayed cyclopropyl substitution at the distal benzyl moiety, wherein the intermediates I3, I4 and I5 are not isolated and/or purified before further processing;
(d) subsequently the cyclopropyl moiety is installed in the corresponding bromo analogue of final intermediate (FI) by means of a transition metal catalyzed reaction with a cyclopropyl species to obtain final intermediate (FI);
(e) final intermediate (FI) is then subjected to the process for the manufacture of the crystalline compound 1-cyano-2-(4-cyclopropyl-benzyl)-4-(β-D-glucopyranos-1-yl)-benzene L-proline monohydrate according to formula (I) according to the following steps:
  (e.1) deacetylating the final intermediate (FI); and
  (e.2) forming the crystalline compound according to formula (I) by reacting the deacetylated final intermediate of step (e.1) with L-proline and water to enable isolation of the final reaction product

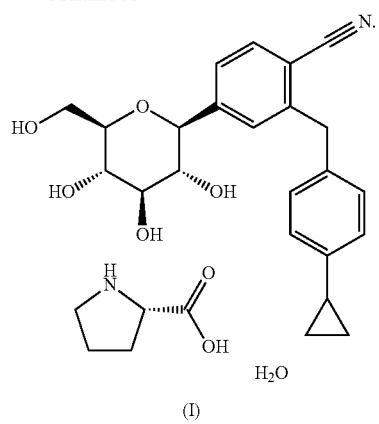

(I)

10. The process according to claim 9 comprising the steps according to the following synthesis route:

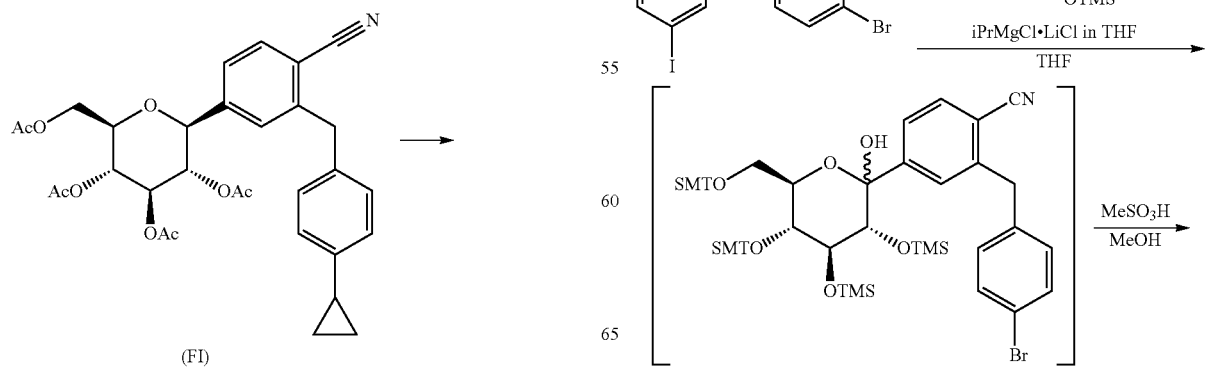

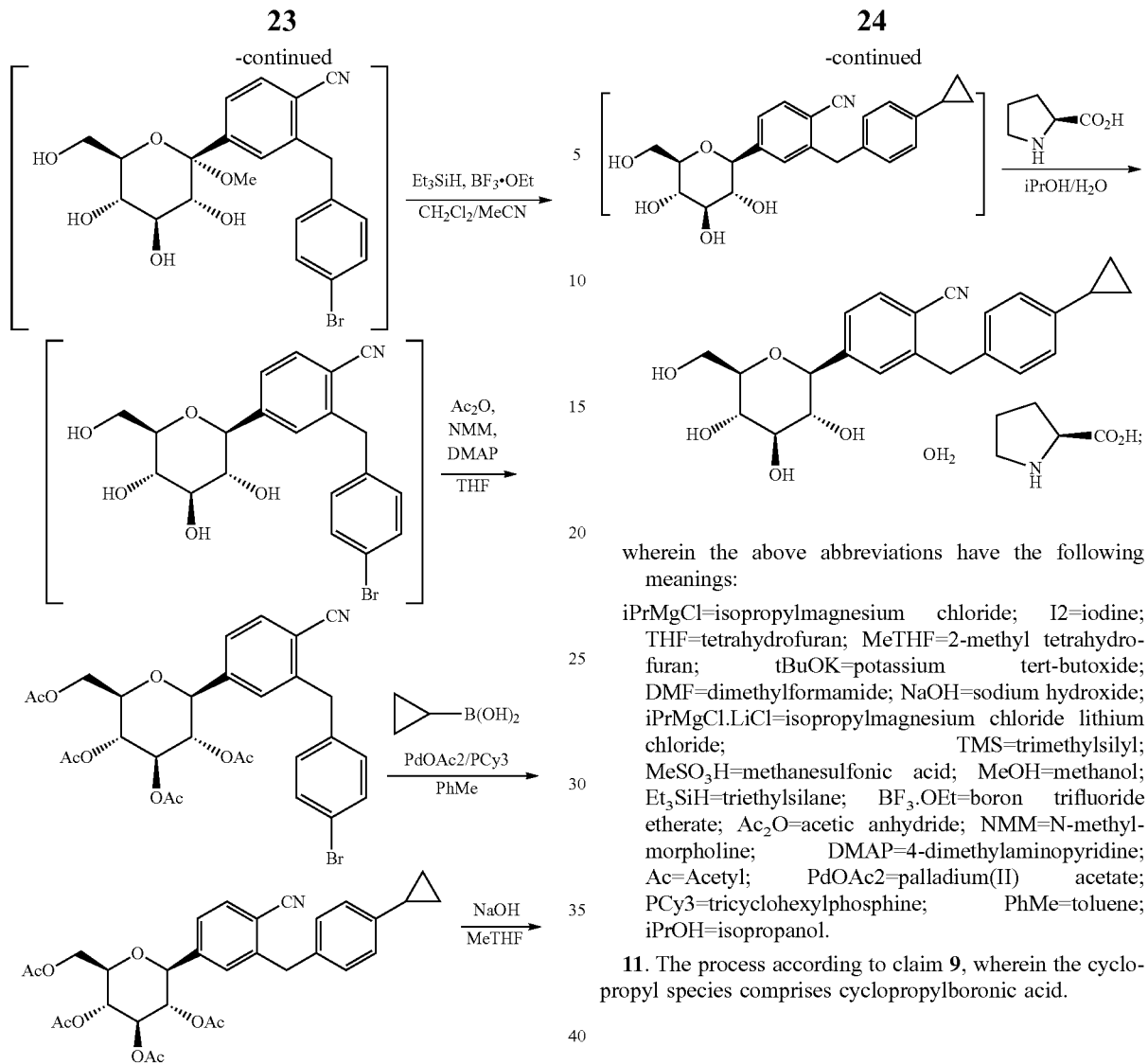

wherein the above abbreviations have the following meanings:

iPrMgCl=isopropylmagnesium chloride; I2=iodine; THF=tetrahydrofuran; MeTHF=2-methyl tetrahydrofuran; tBuOK=potassium tert-butoxide; DMF=dimethylformamide; NaOH=sodium hydroxide; iPrMgCl.LiCl=isopropylmagnesium chloride lithium chloride; TMS=trimethylsilyl; MeSO₃H=methanesulfonic acid; MeOH=methanol; Et₃SiH=triethylsilane; BF₃.OEt=boron trifluoride etherate; Ac₂O=acetic anhydride; NMM=N-methylmorpholine; DMAP=4-dimethylaminopyridine; Ac=Acetyl; PdOAc2=palladium(II) acetate; PCy3=tricyclohexylphosphine; PhMe=toluene; iPrOH=isopropanol.

11. The process according to claim 9, wherein the cyclopropyl species comprises cyclopropylboronic acid.

* * * * *

UNITED STATES PATENT AND TRADEMARK OFFICE
CERTIFICATE OF CORRECTION

PATENT NO. : 11,225,500 B2
APPLICATION NO. : 16/771717
DATED : January 18, 2022
INVENTOR(S) : Eckhardt et al.

Page 1 of 1

It is certified that error appears in the above-identified patent and that said Letters Patent is hereby corrected as shown below:

In the Claims

Columns 17-18 (12) " 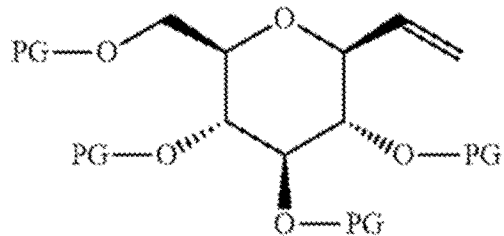 "

Should read -- 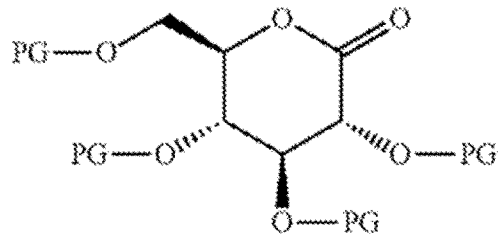 --.

Column 21, Line 30 "acidic reduction/acetylation according to claim 4, steps"
Should read --acidic reduction/acetylation according to claim 1, steps--.

Signed and Sealed this
Twelfth Day of August, 2025

Coke Morgan Stewart
*Acting Director of the United States Patent and Trademark Office*